United States Patent
Santra et al.

(10) Patent No.: US 7,807,265 B2
(45) Date of Patent: Oct. 5, 2010

(54) PARTIALLY PASSIVATED QUANTUM DOTS, PROCESS FOR MAKING, AND SENSORS THEREFROM

(75) Inventors: Swadeshmukul Santra, Orlando, FL (US); Subir Kumar Sabui, Orlando, FL (US); Paul H. Holloway, Gainesville, FL (US); Heesun Yang, Kwanak-Gu (KR)

(73) Assignee: University of Central Florida Research Foundation, Inc., Orlando, FL (US)

( * ) Notice: Subject to any disclaimer, the term of this patent is extended or adjusted under 35 U.S.C. 154(b) by 586 days.

(21) Appl. No.: 11/748,200

(22) Filed: May 14, 2007

(65) Prior Publication Data
US 2007/0264719 A1    Nov. 15, 2007

Related U.S. Application Data

(60) Provisional application No. 60/799,948, filed on May 12, 2006, provisional application No. 60/842,434, filed on Sep. 6, 2006.

(51) Int. Cl.
*B32B 5/16* (2006.01)

(52) U.S. Cl. .................. 428/403; 428/407; 977/773; 977/813; 977/824; 977/834

(58) Field of Classification Search .............. 428/403, 428/407; 977/773, 813, 824, 834
See application file for complete search history.

(56) References Cited

U.S. PATENT DOCUMENTS

| | | | |
|---|---|---|---|
| 6,274,323 B1* | 8/2001 | Bruchez et al. | 435/6 |
| 6,306,610 B1* | 10/2001 | Bawendi et al. | 435/7.1 |
| 6,322,901 B1* | 11/2001 | Bawendi et al. | 428/548 |
| 6,548,168 B1* | 4/2003 | Mulvaney et al. | 428/402 |
| 6,660,381 B2* | 12/2003 | Halas et al. | 428/403 |
| 6,662,671 B1* | 12/2003 | Kopp et al. | 73/865.8 |
| 7,125,605 B2* | 10/2006 | Bawendi et al. | 428/403 |
| 7,198,847 B2* | 4/2007 | Naasani | 428/403 |
| 7,235,361 B2* | 6/2007 | Bawendi et al. | 435/6 |
| 7,253,452 B2* | 8/2007 | Steckel et al. | 257/103 |
| 7,326,908 B2* | 2/2008 | Sargent et al. | 250/214.1 |
| 7,374,824 B2* | 5/2008 | Bawendi et al. | 428/570 |
| 7,410,379 B1* | 8/2008 | Byrne | 439/215 |
| 7,534,489 B2* | 5/2009 | Ying et al. | 428/402 |
| 7,566,476 B2* | 7/2009 | Bawendi et al. | 427/216 |

OTHER PUBLICATIONS

Bronson, et al., "Efficient Immobilization of a Cadmium Chemosensor in an Thin Film: Generation of a Cadmium Sensor Prototype", Organic Letters, vol. 7, No. 6, 2005.

Dabbousi, et al., "(CdSe)ZnS Core-Shell Quantum Dots: Synthesis and Characterization of a Size Series of Highly Luminescent Nanocrystallites", Journal of Physical Chemistry B,1997.

(Continued)

*Primary Examiner*—H. (Holly) T Le
(74) *Attorney, Agent, or Firm*—Jetter & Associates, P.A.

(57) ABSTRACT

A partially passivating core shell particle includes a luminescent nanocrystal core, and a partially passivating semiconducting core shell on a surface of the nanocrystal. The shell allows selected analytes to alter a luminescent response of the core shell particle. A quantum dot-based sensing system includes at least one partially passivating core shell particle, a light source for irradiating the partially passivating core shell particle, and a light detector for receiving emissions from the particle, wherein emissions from the core shell particle change in response to the presence of at least one analyte.

17 Claims, 8 Drawing Sheets

OTHER PUBLICATIONS

Artemyev, et al., "Luminescence of CdS Nanoparticles Doped with Mn", Physica Status Solidi (B), Basic Research, vol. 224, Issue 1, pp. 191-194, Mar. 2001.

Gao, et al., "Quantum-dot Nanocrystals for Ultrasensitive Biological Labeling and Multicolor Optical Encoding", Journal of Biomedical Optics, vol. 7, No. 4, Oct. 2002.

Miller, et al., "A Selective Fluorescent Sensor for Detecting Lead in Living Cells", Journal of American Chemical Society, 2006.

Yoon, et al., "Screening Mercury Levels in Fish with a Selective Fluorescent Chemosensor", Journal of American Chemical Society, 2005.

* cited by examiner

Synthesis of CdS:Mn/ZnS Core/Shell Quantum Dots:

| Qdot Sample ID | [Zn2+ /Cd2+] Initial (Calculated) | Cd actetate + Mn acetate + water + AOT + heptane | Sodium sulfide + water + AOT + heptane | Zn acetate + water + AOT + heptane | Microemulsion Volume (ml) |
|---|---|---|---|---|---|
| QD 1 | 8 | A (= 96 mg + 1.24mg + 3.6 ml + 8.92 g + 100 ml) | B (= 562.4 mg + 10.8 ml + 26.76 g + 300 ml) | C (= 528.4 mg + 10.8 ml + 26.76 g + 300 ml) | 700 |
| QD 1-4 | 8 | A/4 | B/4 | C/4 | 175 |
| QD 1-8 | 8 | A/8 | B/8 | C/8 | 87.5 |
| QD 1-16 | 8 | A/16 | B/16 | C/16 | 43.75 |
| QD 1-20 | 8 | A/20 | B/20 | C/20 | 35 |

F.W. (Cd-acetate: 266.52; Mn-acetate: 245.09; Zn-acetate: 183.48)

Synthesis of CdS:Mn/ZnS Core/Shell Quantum Dots: Controlling crystal growth via scale-down approach

| Qdot Sample ID | [Zn$^{2+}$/Cd$^{2+}$] Initial (Calculated) | [Zn$^{2+}$/Cd$^{2+}$] Final (XPS data) | Microemulsion Volume (ml) | Luminescence intensity at 584 nm (355 nm excitation)* | Luminescence intensity at 584 nm (370 nm excitation)* |
|---|---|---|---|---|---|
| QD 1 | 8 | 6.02 | 700 | 2635600 | 2554610 |
| QD 1-4 | 8 | 8.17 | 175 | 5259010 | 5110030 |
| QD 1-8 | 8 | 11.13 | 87.5 | 713650 | 667160 |
| QD 1-16 | 8 | 3.31 | 43.75 | 618610 | 593390 |
| QD 1-20 | 8 | 8.58 | 35 | 1498800 | 1344270 |

*Qdots were dispersed in 3 ml heptane + 100 µl W/O microemulsion.

PARTIALLY PASSIVATED QUANTUM DOTS, PROCESS FOR MAKING, AND SENSORS THEREFROM

CROSS-REFERENCE TO RELATED APPLICATIONS

The present application incorporates by reference and claims priority to U.S. Provisional Patent Application Ser. No. 60/799,948, entitled "PARTIALLY PASSIVATED QUANTUM DOTS, PROCESS FOR MAKING, AND SENSORS THEREFROM" filed May 12, 2006, and U.S. Provisional Patent Application Ser. No. 60/842,434, entitled "PARTIALLY PASSIVATED QUANTUM DOTS, PROCESS FOR MAKING, AND SENSORS THEREFROM" filed Sep. 6, 2006.

STATEMENT REGARDING FEDERALLY SPONSORED RESEARCH OR DEVELOPMENT

Not applicable.

FIELD OF THE INVENTION

The invention is related to core/shell quantum dots, as well as sensors and methods of sensing analytes utilizing the same.

BACKGROUND OF THE INVENTION

A quantum dot (Qdot) is a semiconductor crystal whose size is on the order of just a few nanometers. Qdots contain anywhere from 100 to 1,000 essentially free electrons and range from about 2 to 10 nanometers in size, or about 10 to 50 atoms, in diameter.

One of the optical features of excitonic Qdots noticeable to the unaided eye is coloration. While the material which makes up a quantum dot is significant, more significant in terms of coloration is the size. The larger the Qdot, the redder (the more towards the longer wavelength end of the electromagnetic spectrum) they fluorescence. The smaller the dot, the bluer (the more towards the short wavelength end) it is. The coloration is directly related to the energy levels of the Qdot. Quantitatively speaking, the bandgap energy that determines the energy (and hence color) of the fluoresced light is approximately inversely proportional to the square of the size of the Qdot. Larger Qdots have more energy levels which are more closely spaced. This allows the Qdot to absorb photons containing less energy, i.e. those closer to the red end of the spectrum.

Regarding fabrication, in semiconductors, Qdots are small regions of one material buried in another with a larger energy (band) gap. Qdots sometimes may occur spontaneously in quantum well structures due to monolayer fluctuations in the well's thickness. Self-assembled quantum dots nucleate spontaneously under certain conditions during molecular beam epitaxy (MBE) and metallorganic vapor phase epitaxy (MOVPE), when a material is grown on a substrate to which it is not lattice matched.

Being quasi-zero dimensional, quantum dots have a sharper density of states than higher-dimensional structures. As a result, they generally have superior transport and optical properties, and are currently being researched for use in diode lasers, amplifiers, and certain biological sensors.

More than a decade-long studies on colloidal luminescent Qdots have revealed that effective surface passivation is critical in making Qdots extremely bright and photostable. Continuous passivation coatings of sufficient thickness thus provide a reduction in the sensitivity of Qdots to various environmental conditions. As a result, Qdots are often passivated with a continuous coating to form core/shell structure comprising an encapulating shell having the Qdot core within.

SUMMARY

A partially passivating core shell particle comprises a luminescent nanocrystal core, and a partially passivating semiconducting core shell on a surface of the nanocrystal. The shell is operable to allow selected analytes to alter a luminescent response of the core shell particle.

In one embodiment, the nanocrystal comprises a metal chalcogenide and the shell comprises a compositionally different metal chalcogenide. In this embodiment, the nanocrystal can comprise CdS and the core shell can comprise ZnS or ZnSe.

The nanocrystal can include a transition or lanthanide metal dopant. In one embodiment, the partially passivating core shell provides a band gap of at least 4 eV at 25 C. The composition can further comprise an analyte selective shell covalently attached to the core shell, such as a Macro-Cyclic Crown Ligand (MCCL).

A quantum dot-based sensing system comprises at least one partially passivating core shell particle including a luminescent nanocrystal core, and a partially passivating semiconducting core shell on a surface of the nanocrystal. The shell allows selected analytes to alter a luminescent response of the core shell particle. A light source is provided for irradiating the partially passivating core shell particle. A light detector receives emissions from the partially passivating core shell, wherein the emissions change in response to the presence of at least one analyte. The system can further comprise at least one optical fiber including a transmitting leg and a receiving leg, and a core portion located between the transmitting leg and the receiving leg covered with at least one of the partially passivated core shell particles. In one embodiment, an analyte selective shell is covalently attached to the partially passivating core shell, such as a MCCL.

The nanocrystal can comprise a metal chalcogenide and the partially passivating core shell can comprise a metal chalcogenide. In one embodiment, the nanocrystal comprises CdS and the partially passivating core shell comprises ZnS or ZnSe.

A method of sensing analytes comprising the steps of providing at least one partially passivating core shell particle comprising a luminescent nanocrystal core and a partially passivating semiconducting coating shell on a surface the nanocrystal, wherein the shell allows selected analytes to alter a luminescent response of the core shell particle. A fluid suspected of including at least one analyte is exposed to the partially passivating core shell particle. Based on a change in luminescent response of the core shell particle following exposure to the fluid it is determined whether the analyte is present in the fluid. The fluid can comprise water. The analyte can be a heavy metal cation, such as Hg, Cd or Pb.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

The present invention is more particularly described in the following description and examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of". In addition, unless indicated otherwise, a description of a layer being disposed on another layer, includes both embodiments where the layer is directly on the other layer or the layer has one or more intermediate layers interposed between the layer and the other layer.

As noted in the Background, it is well known to provide surface passivation layers for Qdots to achieve maximum brightness. Besides providing maximum brightness, such conventional passivation coatings are designed to also provide a reduction in the sensitivity of Qdots to various environmental conditions. Significantly, however, the Inventors have unexpectedly found that a partially passivating semiconductor coating layer disposed on the luminescent nanocrystal dot core which provides a significantly lower brightness compared to a fully passivated layer, provides useful sensing properties that can be used for a variety of chemical/biological sensing applications.

Figure 1:
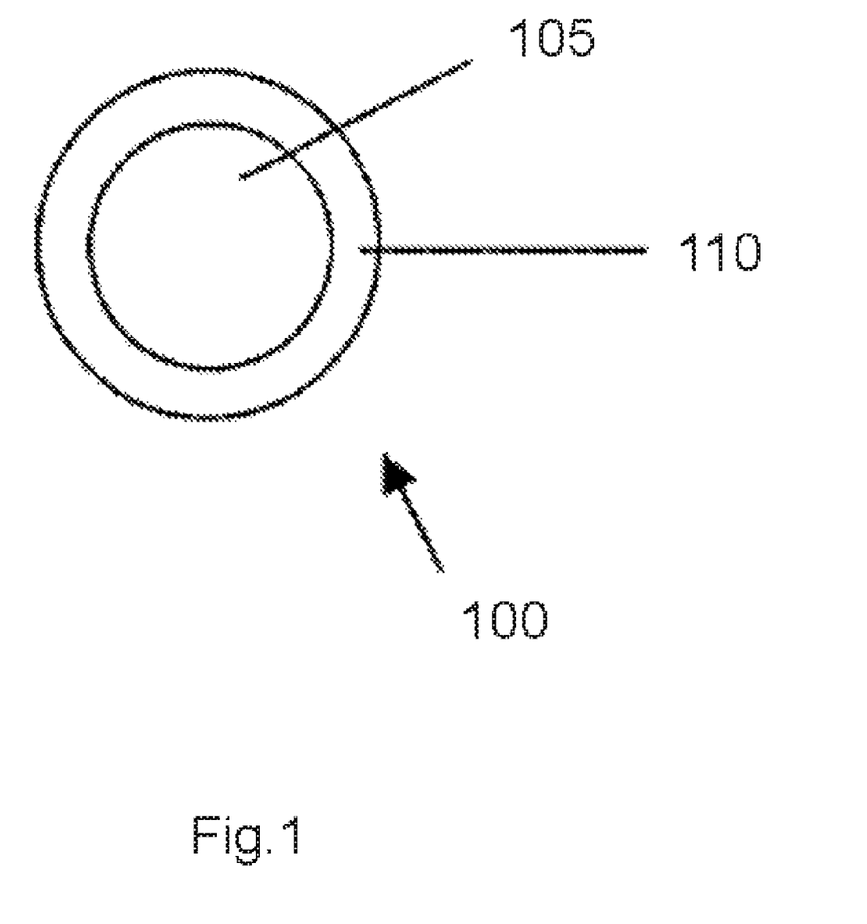
FIG. 1 is a schematic representation of a partially passivated quantum dot (partially passivated Qdot) according to an embodiment of the invention.

A partially passivating core shell particle according to the present invention comprises one or more partially passivated quantum dots. FIG. 1 shows an exemplary partially passivated quantum dot 100 according to an embodiment of the present invention. The nanocrystal core 105 has an average size less than 100 nm, generally being about 1 to 10 nm in size. A partially passivating semiconductor coating layer 110 is disposed on the surface of the luminescent nanocrystal core. As used herein, "partially passivated layer" or "partially passivating layer" is defined by reference to its luminescence intensity measured at the emission band (e.g. 590 nm for Mn doped CdS) as compared to the luminescence intensity of both a fully (optimal) passivated Qdot control and an unpassivated control. Specifically, partially passivated Qdots according to the present invention as defined herein to provide a luminescence intensity range as follows:

i) a maximum intensity level that is at least 30% less than the luminescence of a fully (optimal) passivated Qdot control, and ii) a lower intensity level that is the greater of 85% less that the luminescence of the same fully passivated Qdot control and 30% more than the luminescence intensity of an unpassivated control.

The thickness of the semiconductor coating 110 is generally one to two atomic layers, but can be somewhat thicker, such as three to five atomic layers. The coating is preferably a wide band gap semiconductor, selected to have a larger band gap, such as 0.5 to 1 eV higher, as compared to the band gap provided by the core nanoparticle 105. The partially passivated surface coating according to the present invention exposes at least a portion of the exterior of the luminescent nanocrystalline material to external influences. Although shown in FIG. 1 as being a continuous coating, the surface coating can be discontinuous as well. The semiconductor coating 110 can be a luminescent or non-luminescent coating.

Although not required to practice the present invention, Applicants, not seeking to be bound by theory, believe that by using luminescent core nanoparticles having a significant portion of their surface area exposed to external influences allows certain materials to change the electron-hole recombination process behavior, which results in a change in the photoluminescence (PL) response. Through interaction of the luminescent nanocrystalline material with certain outside influences, and a resulting change in photoluminescence (PL) intensity or PL lifetime, certain outside influences can thus be sensed and identified based on unique PL signatures for a variety of analytes.

Although generally described using a CdS core and a ZnS coating, the invention is in no way limited to any particle luminescent nanocrystalline material or coating. Although the passivating coating is generally an inorganic layer, organic layers may also be used. In some embodiments, the luminescent nanocrystals can be doped with a transition or lanthanide metal.

In one specific embodiment, the luminescent nanocrystalline material is a doped metal chalcogenide, such as Mn doped CdS. CdS:Mn nanocrystals have been found to show efficient and broad photoluminescence (PL) around 2.1 eV. Similar PL is observed in bulk CdS:Mn. This is attributed to the intra-3d transition of $Mn^{2+}$ ions. Moreover, the PL excitation spectrum of CdS:Mn nanocrystals has been found to be similar to the absorption spectrum of CdS nanocrystals. These observations suggest that efficient energy transfer of carriers occurs from CdS nanocrystals to $Mn^{2+}$ ions.

As a result of partial surface passivation according to the present invention, compositions according to the invention behave as if the emission is internally quenched. This arrangement and the discovery of an efficient method to form partially passivating semiconductor coating layers disposed on the luminescent nanocrystals (described below) allows the formation of new Qdot-based analyte sensors. Such sensors have been found to provide high levels of sensitivity toward pH, various metal ions (including bivalent Cd, Pb, Hg cations) and certain organic molecules, and are expected to provide selectivity for organics including nitroaromatic explosives, such as TNT. It is expected that environmentally-sensitive Qdots will also have potential for the biosensing. For example, alteration in the Qdot PL signature is expected once reactive oxygen species (such as associated with superoxide, nitric oxide and peroxide) will interfere with the electron-hole recombination processes at the surface of the luminescent nanoparticle. Accordingly, portable heavy metal detection devices for Hg, Pb, As, Cd ions (samples including contaminated water) can make use of fluorescence signatures upon exposure to heavy metals.

Regarding heavy metal detection using partially passivated Qdots according to the invention, results obtained described below indicated significant sensitivity. Moreover, such Qdots were found to be extremely photostable in solution as was confirmed by the continuous exposure to 450 W Xenon excitation for several hours. However, in certain applications where multiple analytes may be present, such Qdots may not have sufficient selectivity. For instance, when exposed to both $Hg^{2+}$ and $Pb^{2+}$, luminescence quenching of the 584 nm $Mn^{2+}$ $4T_1$-$^6A_1$ band was observed in each case. Moreover, an unknown contaminated soil or water sample may contain various cationic and anionic species, other than toxic heavy metal ions. In this situation, it would be challenging to selectively detect any specific heavy metal.

Figure 2:
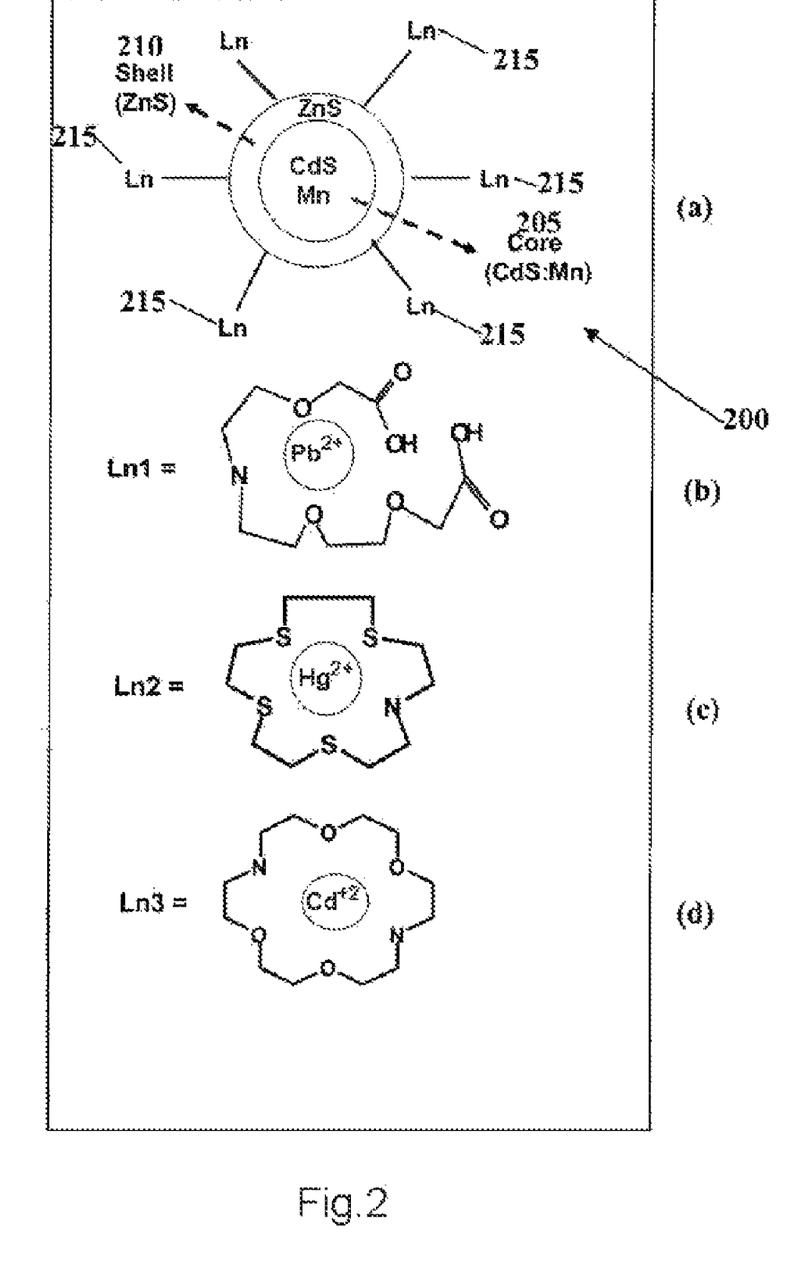
FIG. 2(a) is a schematic representation of an exemplary Qdot-based Heavy Metal Detection Probe (QHMDP) according to the present invention. The QHMDP has a core-shell structure. The shell comprises Macro-Cyclic Crown based Ligands (shown as "Ln") capable of binding to specific heavy metal ions and a large energy gap material (e.g. ZnS) partially passivating a Qdot core. The MCCLs at least partially encapsulate the partially passivateds core.
FIG. 2(b)-(d) show some exemplary MCCLs, shown as Ln1, Ln2 and Ln3, respectively.

To improve selectivity of partially passivated Qdots according to the invention, a new core-shell-shell QHMDP design was developed by the present Inventors. Although described below as being a shell to improve heavy metal selectivity, selectivity enhancing shells can be used to improve selectivity for a variety of non-heavy metal analytes The core here is defined to be a partially passivated core/shell Qdot according to the present invention and is designed to achieve high optical sensitivity (e.g. luminescence quenching of Mn doped CdS 584 nm emission for both $Hg^{2+}$ and $Pb^{2+}$ ions). In one embodiment, The Qdot shell will be synthesized by covalently attaching the core to heavy metal selective ligands, such as Macro-Cyclic Crown Ligands (MCCLs), to provide a Qdot based Heavy Metal Detection Probe (QHMDP) 200 according to the present invention, as shown in FIG. 2(a). QHMDP 200 is shown having a Mn doped CdS core 205, a partially passivating ZnS coating 210, and a plurality of selective ligands 215 (shown as Ln) bound to the ZnS coating 210. In one embodiment the selective ligands 215 are MCCL which are designed to capture specific heavy metals from a mixture heavy metal ions. It is noted that the MCCL or other selective ligands 215 is preferably directly attached to the Qdot surface without a spacer. The purpose for direct attachment is to obtain essentially zero-space surface passivation that will create a non-flexible MCCL coating. In the case of a MCCL coating, such a robust coating should prevent undesired metal ions diffusion to the core. The shell design shown reduces interference due to non-specific binding of undesired metal ions. In a practical situation, however, there will always be a chance of non-specific interaction once the probe is allowed to interact with the sample for a longer period of time. Therefore, when implementing a detection method using QHMDPs according to the present invention, a brief exposure (e.g. <1 minute) of QHMDP to the sample and rapid detection procedure will generally be desirable.

FIGS. 2(b)-(d) show exemplary MCCL coatings for the selective detection of $Pb^{+2}$, $Hg^{+2}$, and $Cd^{+2}$. Although generally covalently attached, it is possible to attach MCCLs to Qdots according to the present invention by certain non-covalent means. Ln1 shown in FIG. 2(b) is not a fully closed ring. As shown in FIG. 2(b)-(d), the MCCLs (e.g. Ln1, Ln2 and Ln3) are shown surrounding their respective selective analytes, $Pb^{+2}$, $Hg^{+2}$, and $Cd^{+2}$, respectively.

MCCLs have been widely used in separation chemistry and treatment of heavy metal poisoning. During the past two decades, several synthetic strategies have been developed to make metal selective MCCLs. Crown ether based chemosensors for the specific detection of Hg (shown in FIG. 2(c)) are disclosed in Yoon, S., et al., Screening mercury levels in fish with a selective fluorescent chemosensor. Journal of the American Chemical Society, 2005. 127(46): p. 16030-16031; hereafter "Yoon et al."]. Crown ether based chemosensors for the specific detection of Pb (shown in FIG. 2(b)) are disclosed in He, Q. W., et al., A selective fluorescent sensor for detecting lead in living cells. Journal of the American Chemical Society, 2006. 128(29): p. 9316-9317; hereafter "He et al."] at trace amounts in living species (e.g. mercury ion detection in fish, intra-cellular lead ion detection in HEK cells). In the chemosensor design disclosed in Yoon et al., a fluorescent reporter molecule (e.g. fluorescein) was covalently attached to a heavy metal specific MCCL ligand. The fluorescein emission was internally quenched in this construct. Upon binding to heavy metal ions, the fluorescein emission was restored. The increase in the emission intensity was directly proportional to the toxic heavy metal ion concentration. The restoration of fluorescein emission clearly indicated that the binding of heavy metals has a direct influence on the electronic states of the fluorescent reporter molecule, drastically reducing non-radiative pathways.

The present invention replaces fluorescein reporter molecules with highly-sensitive, photostable and environmentally sensitive Qdot probes according to the invention. For example, for the detection of $Cd^{2+}$, Ln3 (FIG. 2(d) can be used. Ln3 shown in FIG. 2(d) is disclosed in Bronson et al. [Bronson, R. T., et al., *Efficient immobilization of a cadmium chemosensor in a thin film: Generation of a cadmium sensor prototype*. Organic Letters, 2005. 7(6): p. 1105-1108].

The present invention can be used in a variety of sensor systems. Sensor systems generally comprise a light source for irradiating the partially passivated Qdots. A light detector is provided for receiving emissions (typically fluorescence) from the nanocrystals, wherein the emissions change (intensity, wavelength, decay time) in response to the presence of at least one analyte. A detector for measuring electrical conductivity of the nanocrystals can also be included. The analyte can be in liquid or vapor form. The nanocrystals can be secured to a surface or held in solution. For example, the nanoparticles can be arranged on a packed bead bed or in a particle dispersion on a substrate. In another embodiment, selective shell covered partially passivated Qdots according to the invention are dip coated inside the core of a fiberoptic fiber.

Figure 3A:
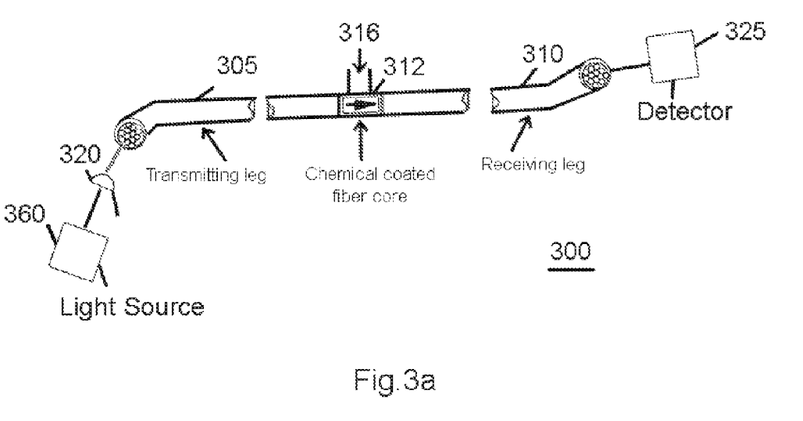
FIGS. 3(a) and (b) show simplified representations of an intrisic and an extrinsic fiber optic based sensor system, respectively, according to an embodiments of the present invention.

FIG. 3(a) shows an intrinsic fiber-optic based hand-held sensor probe 300 according to an embodiment of the present invention. The fiber includes a transmitting leg 305 and a receiving leg 310. Between the transmitting leg 305 and a receiving leg 310 is a core portion 312 having at least one, and generally a plurality of selective shell covered partially passivated Qdots according to the invention coated inside to provide analyte specificity. An inlet region 316 to core region 312 is provided for introducing samples suspected of including one or more targets. A light source (e.g. laser) 315 and lens 320 are provided for coupling light into the transmitting leg 305 of the fiber. A detector 325 is coupled to the output of receiving leg 310. Although not shown, a supervisory computer and processor is preferably included for characterizing the luminescence intensity and/or luminescent lifetime and determining whether a specific analyte is present. By providing multiple fibers all having different selective shells between light source/lens and detector, probes according to the present invention can be used to simultaneously sense a plurality of different analytes.

Figure 3B:
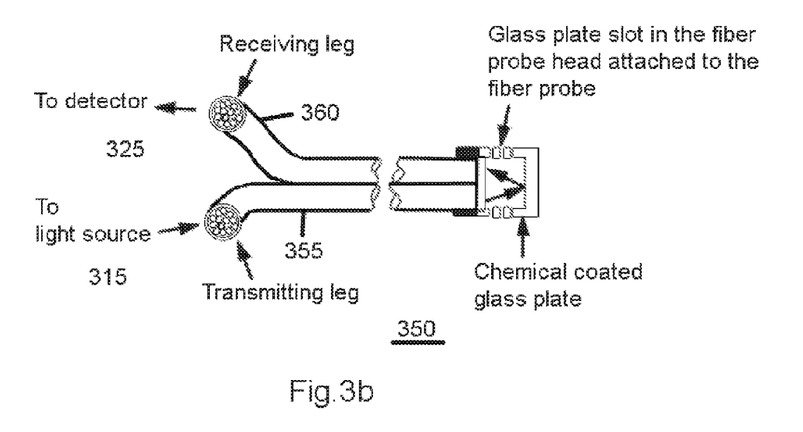

FIG. 3(b) shows an extrinsic fiber-optic based hand-held sensor probe 350 according to an embodiment of the present invention. The fiber includes a transmitting leg 355 and a receiving leg 360. Probe 350 includes positions for insertion of plates having selective shell covered partially passivated Qdots according to the invention coated thereon. As with FIG. 3(a), although not shown, a supervisory computer and processor is preferably included for generating a luminescence spectrum from data provided and determining whether a specific analyte is present. Probes according to the invention are expected to rapidly and selectively detect toxic heavy metal ions at trace levels, such as in the range between parts per billion (ppb) or parts per trillion (ppt).

Besides detecting highly toxic heavy metal ions ($Cd^{2+}$, $Hg^{2+}$, $Pb^{2+}$ and $As^{3+}$ ions), biological reactive species (nitric oxide, super oxide and peroxides), or explosives (e.g. explosive nitro-aromatics) as noted above, nanosensors according to the present invention can also be useful for detection of sodium, potassium, magnesium ions, as well as amino acids and other materials.

Reactive oxygen species (ROS), such as superoxide, nitric oxide, and peroxides are of particular interest as they are responsible for oxidative stress and ageing. Superoxides are known to cause oxidative stress and are directly linked to many neurodegerative diseases such as Alzheimer's, Parkinson's, and Huntington's diseases. Nitric oxide (NO) is an important bioregulatory agent in a range of physiological processes from vasodilation and platelet aggregation to neurotransmission and penile erection. In biology, hydrogen peroxide is considered as a reactive oxygen species that could lead to serious tissue damage. Sensitive detection of these ROS is highly desirable for early diagnosis and monitoring disease progression. Superoxide radicals will be generated in solution by the reaction between xanthine oxidase and hypoxanthine, followed by the treatment with Qdots. Sodium (Z)-1-(N,N-diethylamino)diazen-1-ium-1,2-diolate will be used to generate nitric oxide in solution and will then be treated with Qdots. ROS will generally interfere with the electron-hole recombination processes allowing the effect of ROS to be assessed by monitoring PL characteristics (PL emission, PLE and lifetime measurements) of Qdots according to the present invention.

Detection of explosive nitro-aromatics is important for Homeland Security reasons as these materials fall under the category of cheap and dirty explosives. Electron-deficient explosive nitro-aromatics could behave as surface traps for the electron hole recombination process. It is expected that sensitive responses will be provided by partially passivated Qdots according to the invention. Exemplary explosive nitro-aromatics include 2,4,6 trinitrotoluene (TNT), peroxides and picric acid.

A new room temperature operable synthesis protocol allows synthesis of doped semiconductor nanocrystals, such as CdS:Mn nanocrystals, having variety of surface passivation layers, such as a ZnS layer. Through controlling the process as described below, the surface passivation layer can be continuous or sufficiently thin or discontinuous to be partially passivating. Regarding the new process, as demonstrated in the Examples below, solution volume has unexpectedly been found to be a process parameter which enables formation of a partially passivating passivation layer.

Generally, the method comprises the steps of providing a metal ion comprising water-in-oil micellular solution, the metal ion comprising at least a first and a second metal, providing a chalcogenide ion comprising water-in-oil micellular solution, and mixing the metal ion comprising water-in-oil micellular solution and the chalcogenide ion comprising water-in-oil micellular solution, wherein a stoichiometric surplus of the chalcogenide is provided. A plurality of first or second metal chalcogenide nanoparticles are formed. A third metal comprising water-in-oil micellular solution is then sequentially or simultaneously added, wherein a coating comprising the third metal and chalcogenide forms on the plurality of first or second metal chalcogenide nanoparticles. By using a total volume of reactants sufficiently low, generally less than 400 ml, a partially passivating coating layers is formed on the nanoparticles. Nanoparticles formed by the present method also generally include a plurality of surfactant molecules on their outer surface.

Figure 4:
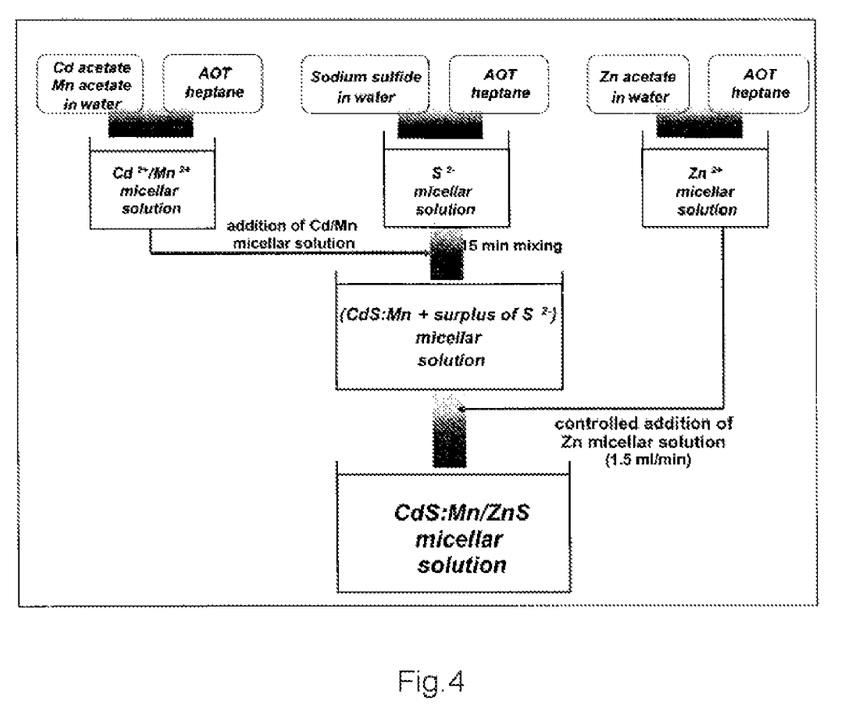
FIG. 4 shows a flow chart for the synthesis of CdS:Mn/ZnS core/shell Qdots using a water-and-oil (W/O) microemulsion according to the invention.

FIG. 4 shows a flow chart for one method suitable for the synthesis of CdS:Mn/ZnS core/shell Qdots using a water-and-oil (W/O) microemulsion according to the invention. In this embodiment, the oil is heptane and the surfactant is sodium dioctyl sulfosuccinate (AOT, 99%, Sigma Chemical Co., St. Louis, Mo.). The water/AOT ratio can be about 10.

EXAMPLES

It should be understood that the Examples described below are provided for illustrative purposes only and do not in any way define the scope of the invention.

While attempting to synthesize CdS:Mn/ZnS Qdots on a small scale (small volume) using a AOT/heptane W/O microemulsion system based on the process described in FIG. 4, an unexpected dramatic scale-down effect of reaction volume on the growth of the ZnS surface passivation layer (shell) onto the CdS:Mn Qdot core was discovered. The Table shown in FIG. 5 described below details the scale-down protocol of Qdot synthesis showing a constant composition using different microemulsion volumes, from about 700 ml to 35 ml.

Figure 6:
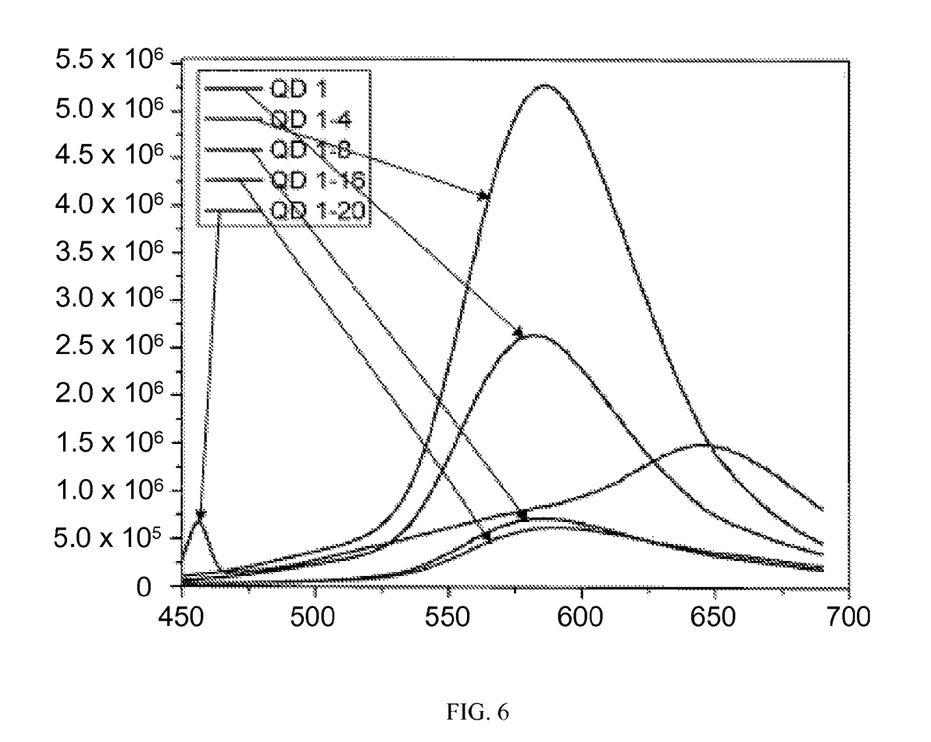
FIG. 6 shows emission spectra for the various Qdot samples showing very significant spectral changes based solely on the microemulsion volume used in the microemulsion system (the scale-down effect).

FIG. 6 shows emission spectra for the various Qdot samples surprisingly showing very significant spectral changes based only the microemulsion volume used in the microemulsion system, referred to herein as the scale-down effect. For all sensing tests 50 μg of nanoparticles were dispersed in 3 ml of methanol along with less than 1% water (V/V). QD1-4 which resulted in a continuous coatings was found to be the brightest. QD1, QD1-8 and QD1-16 which resulted in a partially passivating coating were found to have intermediate (moderate) emission intensity. QD1-20 which resulted in a minimal coating was found to have the lowest emission intensity. Except QD1-20, all samples showed only variation in luminescence intensity at 584 nm, confirming the effect of surface passivation. Sample QD1-20 showed dual emission at 584 nm and 645 nm. The emission at 645 nm could be due to the ionic defect emission (e.g. sulfur vacancies).

As expected, well-surface passivated Qdots showed the brightest intensity and the poorly-passivated Qdots showed very weak emission. However, Qdots with complete surface passivation are expected to be insensitive to the outside environment, while Qdots with partial surface passivation were found to be responsive to the outside environment. As noted above, partially passivated Qdots are believed to possess localized surface states in the band gap as well as ionic defects (e.g. sulfur vacancies in case of CdS:Mn/ZnS Qdots). Therefore, the Inventors determined that the partially passivated Qdots can be used as an environmentally-sensitive probe as it is possible to further quench or enhance the luminescence intensity of the Qdots in the presence of certain analytes.

Several experiments were conducted. Using a dioctyl sulfosuccinate, sodium salt (AOT)/heptane/water W/O microemulsion technique, CdS:Mn core/ZnS shell Qdots were produced based on the process flow described generally in FIG. 4. Typically, $Cd(CH_3COO)_2 \cdot 2H_2O$, $Mn(CH_3COO)_2$, $Na_2S$, and $Zn(CH_3COO)_2$ were used for the preparation of ($Cd^{2+}$+ $Mn^{2+}$), $S^{2-}$, and $Zn^{2+}$ containing the standard aqueous solutions. Each aqueous solution was stirred with an AOT/heptane solution, forming the micellar solution. Mn doped CdS core nanocrystals were formed by mixing ($Cd^{2+}$+$Mn^{2+}$) and $S^{2-}$ containing micellar solutions rapidly for 10-15 min. The $W_0$ value for the W/O microemulsion was 10. For the growth of a shell layer, a $Zn^{2+}$-containing micellar solution was added at a very slow rate (1.5 ml/min) into the CdS:Mn nanocrystal micellar solution (having maintained a surplus of sulfur ions to support the ZnS shell growth). The nucleation and growth of a separate ZnS phase were suppressed by the very slow addition of the $Zn^{2+}$-containing micellar solution.

Figure 5:
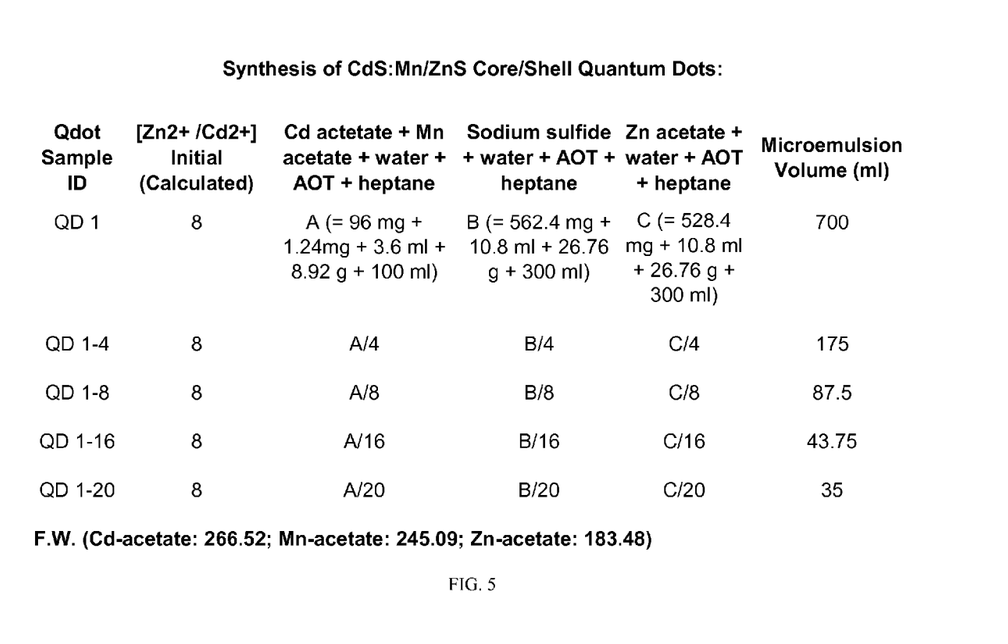
FIG. 5 is a Table showing the experimental protocol used having a constant microemulsion composition to demonstrate a scale-down effect where the microemulsion volume becomes an important process control parameter.

The Table shown in FIG. 5 shows the microemulsion composition used for all samples. Note that in all samples, the relative ratio of $Cd^{2+}$, $Mn^{2+}$, $Zn^{2+}$ and $S^{2-}$ ions are identical. The microemulsion volume was varied from 700 ml (QD1) to 35 ml (QD 1-20). Traditionally, one would expect to obtain Qdots with similar intensities, irrespective of total microemulsion volume. However, the observations obtained showed this was not the case (see FIG. 7 described below). The brightness of sample QD 1-4 was the maximum followed by the gradual decrease in luminescence intensity from QD 1 to QD 1-8 to QD1-16 that showed a yellow emission from $Mn^{2+}$ $^4T_1$-$^6A_1$ transition at the ~584 nm under a hand-held 366 nm multi-band UV light source. It is believed that the QD 1-4 sample had a well-passivating ZnS layer as it showed the brightest Mn emission. X-ray photoelectron spectroscopy (XPS) analysis reported in FIG. 7 described below showed drastic deviation of [$Zn^{2+}$] to [$Cd^{2+}$] molar ratio ($X_0$ value) from the calculated value of 8. $X_0$ values for QD1, QD1-4, QD 1-8 and QD 1-16 samples were 6.02, 8.17, 11.13 and 3.31, respectively. Note that the experimental $X_0$ value of the brightest sample (QD 1-4) was very close to the calculated value (i.e. 8). Fluorescence emission spectra recorded for all samples clearly showed drastic scale-down effect on the surface passivation process of the Qdots as shown in FIG. 6.

Figure 7:
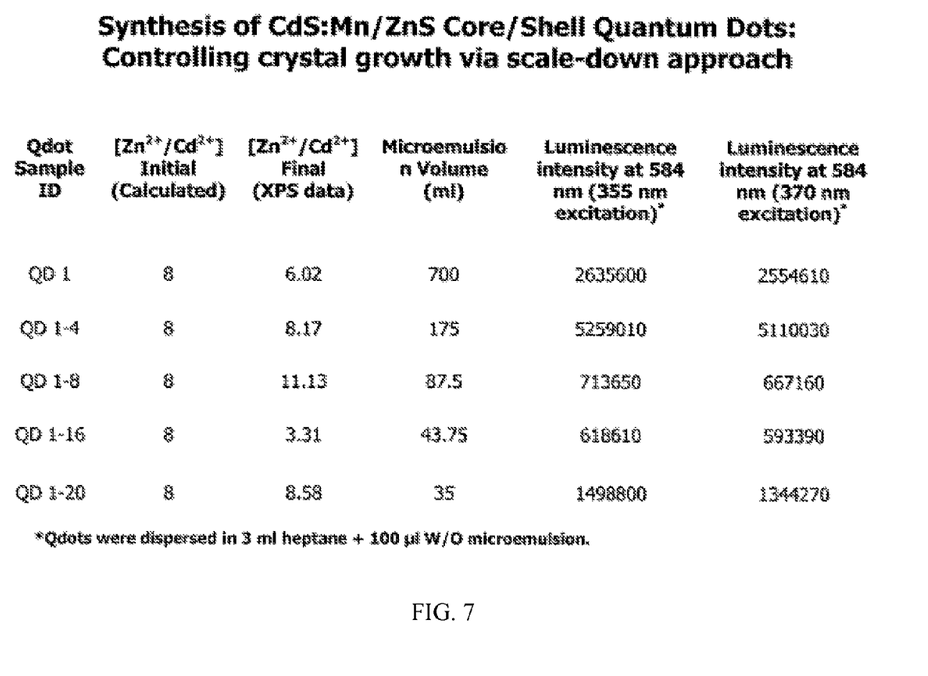
FIG. 7 provides data including XPS data for the various samples described above evidencing a variation in $Zn^{+2}/Cd^{+2}$ ratio between the sample groups.

FIG. 7 provides a table including XPS data for the various samples described above. Significantly, the $Zn^{+2}/Cd^{+2}$ ratio varied from the nominal calculated value of 8, to values above and below 8. A high $Zn^{+2}/Cd^{+2}$ ratio may be evidence of a partially passivated surface.

To demonstrate the environmental sensitivity of partially passivated Qdots according to the invention, QD 1 and QD1-8 were intentionally selected as the test samples as they are about 2 and 7.4 times dimmer than QD 1-4 and thus should be partially surface-passivated. As noted above, for fluorescence measurements, all experimental Qdot solutions (concentration: 50 μg/ml) were prepared at room temperature in methanol containing DI water (maximum 0.01% (V/V)). Again, all experimental Qdot solutions were transparent and no light-scattering was observed in the visible range. When exposed to highly toxic heavy metal ions (e.g. $Cd^{2+}$, $Hg^{2+}$, $Pb^{2+}$ ions etc.), quenching of 584 nm Qdot emission was observed in a unique fashion for each type of metal ion. It was observed that with respect to luminescence quenching, both QD1 and QD1-8 samples had similar response.

Figure 8:
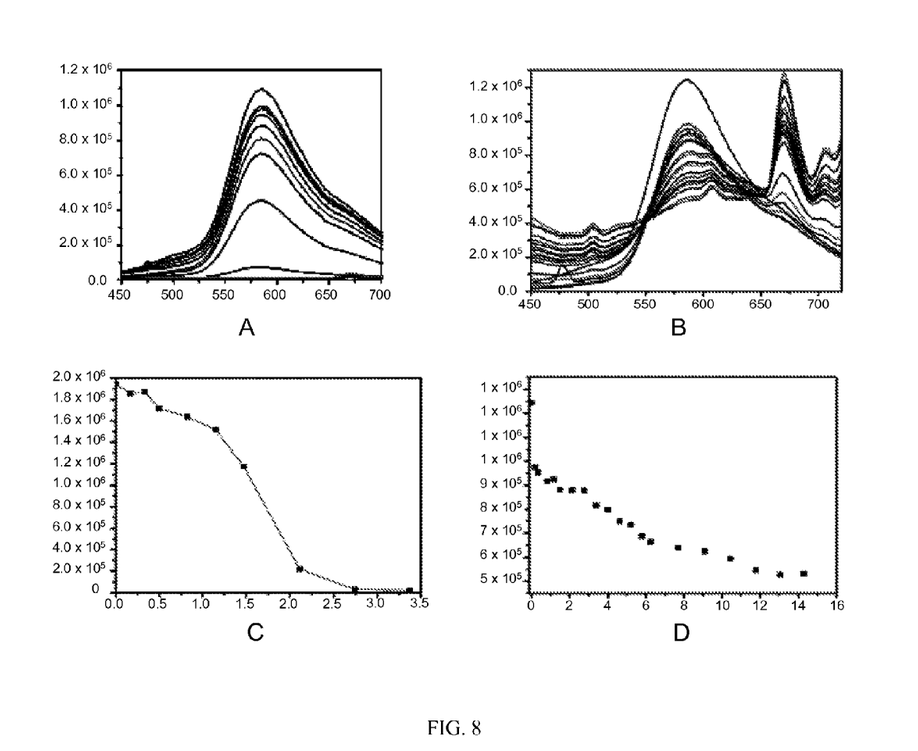
FIG. 8 shows the effect of metal ion concentration on the luminescence intensity for the metal ions $Cd^{+2}$, $Hg^{+2}$ and $Pb^{+2}$, as a function of concentration of the metal ion.

FIG. 8 shows the effect of increased amounts of metal ion concentration on the luminescence intensity of QD1-8. The luminescence quenching efficiency of $Hg^{2+}$ was at least three orders of magnitude higher than $Cd^{2+}$ ions. The higher sensitivity of Qdots towards $Hg^{2+}$ could be attributed to the high reactivity of $Hg^{2+}$ ions towards Qdots, forming metal-like products such as HgS, CdHgS etc. Unlike $Hg^{2+}$ ion, the luminescence intensity of QD1-8 measured at 584 nm increased first, reached a maximum at around 3 mM $Cd^{2+}$ ion concentration, and then decreased. The initial enhancement in luminescence intensity could be due to the formation of the $Cd(OH)_2$ layer over the CdS:Mn partially passivated core, which resulted in the reduction of the non-radiative recombination of charge carriers (electron-hole recombination without luminescence). Further, the decrease in the luminescence intensity with the increase in $Cd^{2+}$ ions could not be explained without further investigation.

Different analytes were found to provide characteristic luminescent signatures as shown in FIG. 8. Once cataloged, such signatures allow unambiguous identification of particular analytes. For example, when exposed to $Pb^{2+}$ ions, the luminescence spectral characteristics of QD1-8 (lower right) was quite different as compared to the spectral characteristics obtained from $Cd^{2+}$ and $Hg^{2+}$ ions (left). For exposure to $Pb^{2+}$, a decrease in emission intensity at 584 nm was noticed and a new emission (upper left) peak at ~643 nm appeared as the $Pb^{2+}$ concentration increased from 0.166 mM to 14.28 mM (upper right). Several control spectral experiments were performed including emission spectra of pure methanol, methanol-water mixture, 14.28 mM $PbCl_2$ in methanol and emission spectra in the presence of room-light to confirm the unusually sharp peak (much like a scattering peak) in the emission spectra. With a 370 nm UV exposure, 643 nm deep-red emission from 14.28 mM $PbCl_2$ treated QD1-8 a sample was seen visually. The emission data obtained demonstrates that partially passivated Qdots can be used as environment sensitive probes which provide identification of specific analytes. To obtain improved selectivity in samples containing several analytes, the Qdot-based Heavy Metal Detection Probes (QHMDP) according to the present invention having Macro-Cyclic Crown based Ligands described above relative to FIGS. 2(b)-(d) can be used.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A core shell particle, comprising:
a luminescent nanocrystal core, and
a partially passivating semiconducting shell on a surface said nanocrystal, and
an analyte selective shell covalently attached to said semiconductor shell.

2. The core shell particle of claim 1, wherein said nanocrystal comprises a metal chalcogenide and said semiconductor shell comprises a compositionally different metal chalcogenide.

3. The core shell particle of claim 2, wherein said nanocrystal comprises CdS and said semiconductor shell comprises ZnS or ZnSe.

4. The core shell particle of claim 1, wherein said nanocrystal includes a transition or lanthanide metal dopant.

5. The core shell particle of claim 1, wherein said semiconductor shell provides a band gap of at least 4 eV at 25° C.

6. The core shell particle of claim 1, wherein said analyte selective shell comprises a Macro-Cyclic Crown Ligand (MCCL).

7. A quantum dot-based sensing system, comprising:
at least one core shell particle including a luminescent nanocrystal core, and
a partially passivating semiconducting shell on a surface said nanocrystal,
an analyte selective shell covalently attached to said semiconductor shell;
a light source for irradiating said core shell particle, and a light detector for receiving emissions from said core shell particle, wherein said emissions change in response to the presence of at least one analyte.

8. The system of claim 7, further comprising at least one optical fiber including a transmitting leg and a receiving leg, and a core portion located between said transmitting leg and said receiving leg covered with at least one of said core shell particles.

9. The system of claim 7, wherein said analyte selective shell comprises a Macro-Cyclic Crown Ligand (MCCL).

10. The system of claim 7, wherein said nanocrystal comprises a metal chalcogenide and said semiconducting shell comprises a compositionally different metal chalcogenide.

11. The system of claim 10, wherein said nanocrystal comprises CdS and said semiconducting shell comprises ZnS or ZnSe.

12. A method of sensing analytes, comprising the steps of:
providing at least one core shell particle comprising a luminescent nanocrystal core and a partially passivating semiconducting shell on a surface said nanocrystal, and an analyte selective shell covalently attached to said semiconductor shell;
exposing a fluid suspected of including at least one analyte to said core shell particle, and
determining whether said analyte is present in said fluid based on a change in luminescent response of said core shell particle following exposure to said fluid.

13. The method of claim 12, wherein said fluid comprises water.

14. The method of claim 12, wherein said analyte is selected from the group of heavy metal cations.

15. The method of claim 14, wherein said heavy metal cation comprises Hg, Cd or Pb.

16. The method of claim 12, wherein when said analyte is present in said fluid said change in luminescent response of said core shell particle following exposure to said fluid comprises an enhanced luminescent response.

17. The method of claim 12, wherein said analyte selective shell comprises a Macro-Cyclic Crown Ligand (MCCL).

* * * * *